(12) United States Patent
Wiley, II et al.

(10) Patent No.: US 7,840,424 B2
(45) Date of Patent: Nov. 23, 2010

(54) SYSTEMS AND METHODS FOR RETAINING OR SHIFTING PRESCRIPTION MARKET SHARE

(75) Inventors: Joseph Lee Wiley, II, Douglasville, GA (US); Kenneth E. Burkett, Southlake, TX (US)

(73) Assignee: NDCHealth Corporation, Atlanta, GA (US)

( * ) Notice: Subject to any disclaimer, the term of this patent is extended or adjusted under 35 U.S.C. 154(b) by 925 days.

(21) Appl. No.: 11/674,069

(22) Filed: Feb. 12, 2007

(65) Prior Publication Data

US 2007/0276697 A1 Nov. 29, 2007

Related U.S. Application Data

(60) Provisional application No. 60/772,461, filed on Feb. 10, 2006.

(51) Int. Cl.
*G06Q 40/00* (2006.01)
*G06Q 30/00* (2006.01)

(52) U.S. Cl. ............................ 705/4; 705/14.1
(58) Field of Classification Search .................. None
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,337,129 | B1 | 2/2008 | Lowry et al. |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |

(Continued)

FOREIGN PATENT DOCUMENTS

CA 2482370 3/2006

(Continued)

OTHER PUBLICATIONS www.ncoil.org/news/DrugCards2.doc dated Apr. 2002.

(Continued)

*Primary Examiner*—Jason M Borlinghaus
(74) *Attorney, Agent, or Firm*—Sutherland Asbill & Brennan LLP

(57) ABSTRACT

Systems and methods are provided for retaining or shifting prescription market share. The systems and methods may include receiving a claim from a pharmacy computer, where the claim is associated with a drug requested by a customer, routing the claim to an adjudication engine for benefits processing, and receiving, from the adjudication engine, coverage information for the claim, where the coverage information indicates an amount payable by the customer. The systems and methods may further include determining whether a discount or payment is available to reduce the amount payable by the customer, where the discount or payment is associated with funding by a pharmaceutical manufacturer. If the discount or payment is available, the systems and methods may include transmitting at least a notice of availability of the discount or payment to the pharmacy computer, or automatically adjudicating the claim back to the pharmacy with the reduced amount payable by the customer.

15 Claims, 10 Drawing Sheets

U.S. PATENT DOCUMENTS

| | | |
|---|---|---|
| 2003/0009367 A1 | 1/2003 | Morrison |
| 2003/0050799 A1 | 3/2003 | Jay et al. |
| 2003/0149625 A1* | 8/2003 | Leonardi et al. .............. 705/14 |
| 2003/0154163 A1 | 8/2003 | Phillips et al. |
| 2003/0229540 A1 | 12/2003 | Algiene |
| 2004/0039599 A1 | 2/2004 | Fralic |
| 2004/0073457 A1 | 4/2004 | Kalies |
| 2004/0078234 A1 | 4/2004 | Tallal |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Patterson et al. |
| 2005/0240473 A1 | 10/2005 | Ayers |
| 2005/0288972 A1 | 12/2005 | Marvin et al. |
| 2006/0020514 A1 | 1/2006 | Yered |
| 2006/0026041 A1 | 2/2006 | Ullman |
| 2006/0149595 A1 | 7/2006 | Williams et al. |
| 2006/0149784 A1 | 7/2006 | Tholl et al. |
| 2006/0184391 A1 | 8/2006 | Barre et al. |
| 2006/0259363 A1 | 11/2006 | Jhetam |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Non-final Office Action for U.S. Appl. No. 12/189,654 mailed Jan. 22, 2010.

Non-final Office Action for U.S. Appl. No. 12/189,650 mailed Jan. 22, 2010.

Sampson, R.J., Taking Control of Health Care Costs, Best's Review—Life Health Insurance Edition, Nov. 1983, pp. 64-66, vol. 84, Issue 7, USA.

Anonymous, ACS to Demostrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescriptions, with the Aim of Cutting Costs, Financial Times, London, Feb. 21, 2001, p. 6, London, United Kingdom.

Anonymous, Pharmacy Industry Leaders Launch Firm to Supply Real-Time Data, PR Newswire, Jul. 30, 2001, p. 1, New York, NY, USA.

Anonymous, Medic: On-line Goes In-House, Chain Store Age Executive, Jan. 1987, pp. 128-132, vol. 63, Issue 1, USA.

Anonymous, TechRx Announces Successful Beta Deployment of T-Rex, PR Newswire, May 13, 2002.

Accelerated Examination Support Document for U.S. Appl. No. 12/189,650 dated Aug. 11, 2008.

Accelerated Examination Support Document for Application No. 12/189,654 dated Aug. 11, 2008.

* cited by examiner

SYSTEMS AND METHODS FOR RETAINING OR SHIFTING PRESCRIPTION MARKET SHARE

RELATED APPLICATION

This application claims priority to U.S. Provisional Ser. No. 60/772,461, entitled "Systems and Methods for Retaining Prescription Market Share," filed on Feb. 10, 2006, which is incorporated by referenced as if fully set forth herein.

FIELD OF THE INVENTION

Aspects of the invention relate generally to prescription drugs, medications, over-the-counter drugs, or medical devices and more particularly, to systems and methods that allow pharmaceutical manufacturers to retain or shift market share for their prescription drugs, medications, over-the-counter drugs, or medical devices (collectively referred to herein as "drugs").

BACKGROUND OF THE INVENTION

With the increasing costs of drugs, customers as a whole are a highly price-sensitive group. Indeed, studies have shown that the likelihood of a customer purchasing drugs is strongly correlated with the customer's out-of-pocket amount for the drugs. As an example, customers may select one drug over another based upon a lower co-pay amount. As another example, a customer may select (or request a prescription for) a drug that is covered by one or more third-party payors (e.g., an insurance plan) as opposed to a drug that is not covered by the third-party payors.

Given that customers are a price-sensitive group, it is not usual to expect that customers may stop taking a drug or may switch to a cheaper drug if the customer's out-of-pocket amount increases. The customer's out-of-pocket amount may increase, for example, where the employer changes the types of drugs that will be covered under a preferred status under its insurance plan. Likewise, a customer's out-of-pocket amount may increase where an insurer or other third-party payor changes the pharmaceutical manufacturers and/or drugs that are preferred. In these situations, the pharmaceutical manufacturers may lose control over the customer's out-of-pocket amount for its drugs, thereby risking that the customer will stop taking its drugs.

Accordingly, there is a need in the industry for systems and methods that enables pharmaceutical manufacturers can retain or shift their drug market share.

SUMMARY OF THE INVENTION

According to an embodiment of the invention, there is a computer-implemented method of retaining or shifting prescription market share. The method may include receiving a claim from a pharmacy computer, where the claim is associated with a drug requested by a customer, routing the claim to an adjudication engine for benefits processing, and receiving, from the adjudication engine, coverage information for the claim, where the coverage information indicates an amount payable by the customer. The method may further include determining whether a discount or payment is available to reduce the amount payable by the customer, where the discount or payment is associated with funding by a pharmaceutical manufacturer, and if the discount or payment is available, transmitting at least a notice of availability of the discount or payment to the pharmacy computer.

According to another embodiment of the invention, there is a computer-implemented method of retaining or shifting prescription market share. The method may include receiving a primary claim from a pharmacy computer, wherein the primary claim is associated with a drug requested by a customer, routing the primary claim to an adjudication engine for benefits processing, and receiving, from the adjudication engine, coverage information for the primary claim, where the coverage information indicates an amount payable by the customer. The method may further include determining whether a discount or payment is available to reduce the amount payable by the customer, where the discount or payment is associated with funding by a pharmaceutical manufacturer, and if the discount or payment is available, storing an indication of the discount or payment for the primary claim and adjudicating the primary claim back to the pharmacy with the reduced amount payable by the customer.

According to yet another embodiment of the invention, there is a system for retaining or shifting prescription market share. The system includes a memory configured to store computer-executable instructions and a processor in communication with the memory. The processor may be operable to execute the computer-executable instructions to receive a claim from a pharmacy computer, where the claim is associated with a drug requested by a customer, route the claim to an adjudication engine for benefits processing, and receive, from the adjudication engine, coverage information for the claim, wherein the coverage information indicates an amount payable by the customer. The processor may be further operable to execute the computer-executable instructions to determine whether a discount or payment is available to reduce the amount payable by the customer, where the discount or payment is associated with funding by a pharmaceutical manufacturer, and if the discount or payment is available, transmit at least a notice of availability of the discount or payment to the pharmacy computer.

According to still another embodiment of the invention, there is a system retaining or shifting prescription market share. The system may include a memory configured to store computer-executable instructions, and a processor in communication with the memory. The processor may be operable to execute the computer-executable instructions to receive a primary claim from a pharmacy computer, where the primary claim is associated with a drug requested by a customer, route the primary claim to an adjudication engine for benefits processing, and receive, from the adjudication engine, coverage information for the primary claim, where the coverage information indicates an amount payable by the customer. The processor may be further operable to execute the computer-executable instructions to determine whether a discount or payment is available to reduce the amount payable by the customer, where the discount or payment is associated with funding by a pharmaceutical manufacturer, and if the discount or payment is available, store an indication of the discount or payment for the primary claim and adjudicating the primary claim back to the pharmacy with the reduced amount payable by the customer.

BRIEF DESCRIPTION OF THE DRAWINGS

Reference will now be made to the accompanying drawings, which are not necessarily drawn to scale, and wherein.

DETAILED DESCRIPTION

Figure 1:
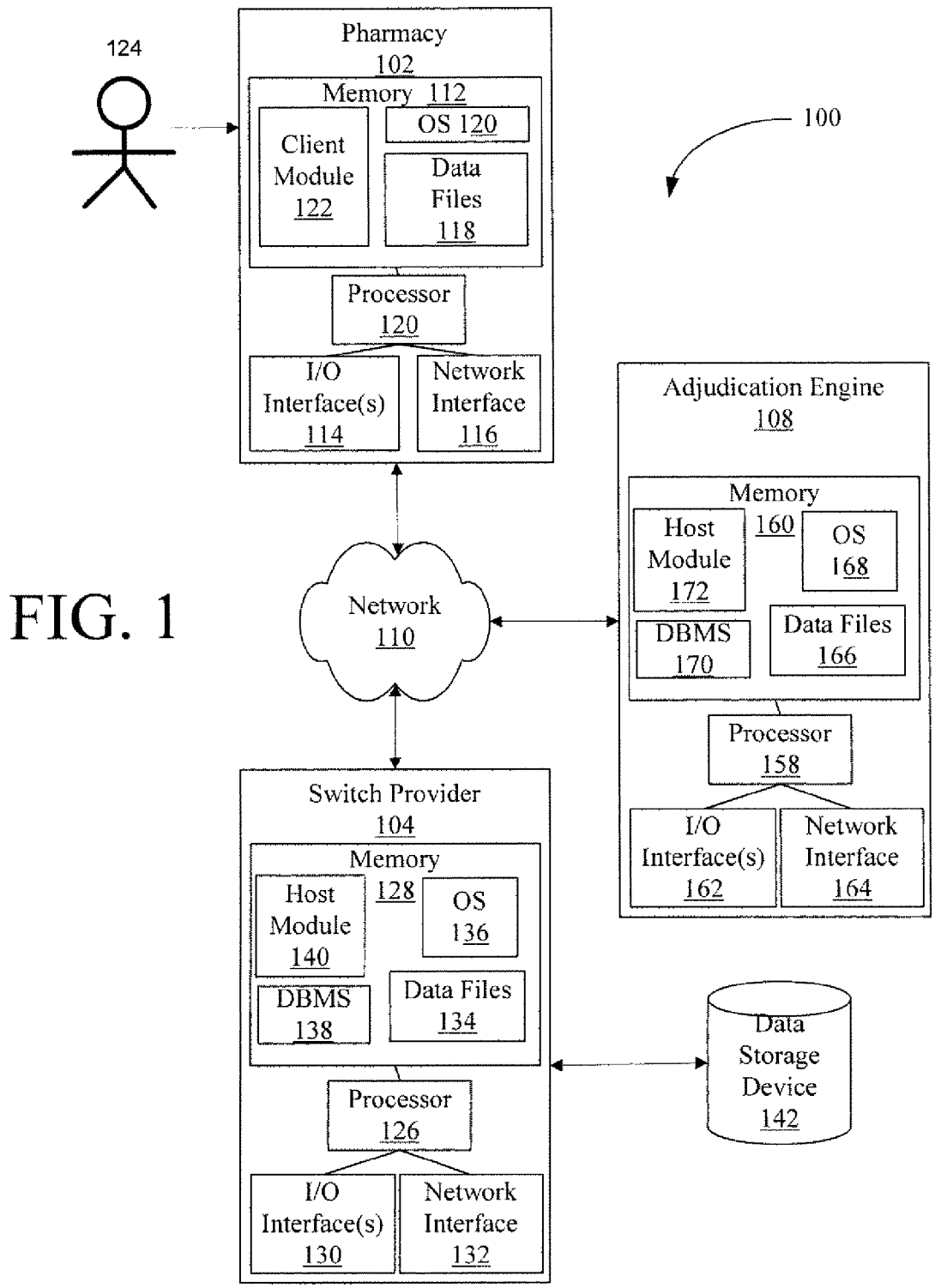
FIG. 1 illustrates an exemplary system that allows a pharmaceutical manufacturer (or other provider) to retain or shift prescription market share, according to an embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data-processing apparatus to cause a series of operational elements or steps to be performed on the computer or other programmable apparatus to produce a computer-implemented process such that the instructions that execute on the computer or other programmable apparatus provide elements or steps for implementing the functions specified in the flowchart block or blocks.

Accordingly, blocks of the block diagrams and flowchart illustrations may support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Embodiments of the invention can provide means and mechanisms by which pharmaceutical manufacturers, or their representatives or providers (collectively referred to sometimes as "pharmaceutical manufacturers") can retain or shift market share for its drugs in the marketplace. According to an exemplary embodiment of the invention, this marketplace may include the 100% co-pay marketplace (e.g., a discount program) and the funded (e.g., insurance plans) marketplace. In the funded marketplace, a customer may still be required to pay a co-pay with each filled drug order. In each of these marketplaces, embodiments of the invention, the drug transactions may be facilitated between a pharmacy and a switch provider, where the switch provider may implement means and mechanisms for incentivising the customer to stay on or shift to a particular drug. It will be appreciated that yet other marketplaces may be available without departing from embodiments of the invention. An exemplary system that allows a pharmaceutical manufacturer to retain or shift its drug market share will now be described illustratively with respect to FIG. 1.

System Overview

FIG. 1 illustrates an exemplary system 100 that allows a pharmaceutical manufacturer to retain or shift its drug market share in the 100% co-pay marketplace (e.g., a discount program) and the funded (e.g., insurance plan, Medicare, etc.) marketplace. In particular, the system 100 includes at least one pharmacy 102 computer, at least one switch provider 104, and an adjudication engine 108, which are each configured for accessing and reading associated computer-readable media having stored thereon data and/or computer-executable instructions for implementing the various methods of the invention. Generally, the adjudication engine 108 may determine benefits, coverage, and/or extent of coverage for one or more claims. According to one embodiment of the invention, the adjudication engine 108 may be associated with a pharmaceutical benefits manager (PBM), which may generally include any third-party payor such as insurance companies, Medicare, and the like. According to another embodiment of the invention, the adjudication engine 108 may also include providers of 100% co-pay plans such as discount programs. According to yet another embodiment of the invention, the adjudication engine 108 may be the switch provider 104.

Generally, network devices and systems, including the one or more pharmacy 102 computers, switch providers 104, and adjudication engines 108 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

Still referring to FIG. 1, a pharmacy 102 computer may be in communication with the switch provider 104 via a network 110, which as described below can include one or more private and public networks, including the Internet. Likewise, the switch provider 104 may also be in communication with an adjudication engine 108 via the network 110. According to an embodiment of the invention, the pharmacy 102 computer, the switch provider 104, and the adjudication engine 108 may be in direct communication with each other. Each of these components—the pharmacy 102 computer, the switch provider 104, the adjudication engine 108, and the network 110—will now be discussed in turn below.

First, the pharmacy 102 computer may be any processor-driven device, such as a personal computer, laptop computer, handheld computer, and the like. In addition to having a processor 112, the pharmacy 102 computer may further include a memory 112, input/output ("I/O") interface(s) 114, and a network interface 116. The memory 112 may store data files 118 and various program modules, such as an operating system ("OS") 120 and a client module 122. The client module 122 may be an Internet browser or other software, including a dedicated program, for interacting with the switch provider 104. For example, a user such as a pharmacist or other pharmacy employee, may utilize the client module 122 in preparing and providing a drug request or order to the switch provider 104 for processing. The pharmacy 102 computer may also utilize the client module 122 to retrieve or otherwise receive data from the switch provider 104, including application or availability of a voucher, coupon, payment and/or discount, as described herein, for the drug request or order.

Still referring to the pharmacy 102 computer, the I/O interface(s) 114 facilitate communication between the processor 110 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy 102 computer will be apparent to those of ordinary skill in the art and are therefore not discussed in more detail herein.

Similar to the pharmacy 102 computer, the switch provider 104 may include any processor-driven device that is configured for receiving, processing, and fulfilling requests or claims from the pharmacy 102 computer related to pharmacy, benefits, and/or discount transactions, including coupons and/or vouchers described herein. The switch 104 may therefore include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. According to an embodiment of the invention, the data files 134 may store history records or tables associated with one or more claim submissions. The data files 134 may also store routing tables for determining the subsequent transmission of received claim submission. For example, these routing tables may determine that particular claim submissions are associated with certain PBMs, and therefore specify a particular adjudication engine 108 to route the claim submissions to. The host module 140 initiates, receives, processes, and responds to requests from the respective client module 122 of pharmacy 102 computer, and further initiates, receives, processes, and responds to requests from the respective host modules 172 of the adjudication engine 108. The switch provider 104 may include additional program modules for performing other pre-processing or post-processing methods described herein. Those of ordinary skill in the art will appreciate that the switch provider 104 may include alternate and/or additional components, hardware or software. According to an embodiment of the invention, the switch provider 104 may be similar to the host server described in U.S. patent application Ser. No. 10/439,422, filed May 16, 2003, and entitled "Systems and methods for verifying and editing electronically transmitted claim content." The foregoing application, which was published on Apr. 22, 2004 as U.S. Publication No. 2004/0078247, is incorporated by reference.

As illustrated in FIG. 1, the switch provider 104 may include or be in communication with at least one data storage device 142, or databases. If the switch provider 104 includes the data storage device 142, then the data storage device 142 could also be part of the memory 128. The data storage device 142 and/or memory 128 may store, for example, program rules and transaction records (e.g., history records) and/or discounts (e.g., coupons, vouchers, etc.) associated with the drug requests and orders. Although a single data storage device 142 is referred to herein for simplicity, those skilled in the art will appreciate that multiple physical and/or logical data storage devices or databases may be used to store the above mentioned data. For security and performance purposes, the switch provider 104 may have a dedicated connection to the data storage device 142. However, the switch provider 104 may also communicate with the data storage device 142 via a network 110, as shown. In other embodiments of the invention, the switch provider 104 may include the data storage device 142 locally. The switch provider 104 may also otherwise be part of a distributed or redundant database management system ("DBMS").

Similarly, the adjudication engine 108 may include any processor-driven device that is configured for receiving, processing, and fulfilling requests from the switch provider 104 related to the pharmacy, benefits, and/or discount transactions. The adjudication engine 108 may therefore include a processor 158, a memory 160, input/output ("I/O") interface(s) 162, and a network interface 164. The memory 160 may store data files 166 and various program modules, such as an operating system ("OS") 168, a database management system ("DBMS") 170, and the host module 172. The host module 172 initiates, receives, processes, and responds to requests from host module 140 of the switch provider 104. The adjudication engine 108 may include additional program modules for performing other pre-processing or post-processing methods described herein. Those of ordinary skill in the art will appreciate that the adjudication engine 108 may include alternate and/or additional components, hardware or software.

The network 110 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 110 may also allow for real-time, off-line, and/or batch transactions to be transmitted between the pharmacy 102 computer and the switch provider 104. Due to network connectivity, various methodologies as described herein may be practiced in the context of distributed computing environments. Although the pharmacy 102 computer is shown for simplicity as being in communication with the switch provider 104 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices of the invention. According to an embodiment of the invention, the network 110 may include a network similar to NDCHealth's Intelligent Network.

Those of ordinary skill in the art will appreciate that the system 100 shown in and described with respect to FIG. 1 is provided by way of example only. Numerous other operating environments, system architectures, and device configurations are possible. Accordingly, the invention should not be construed as being limited to any particular operating environment, system architecture, or device configuration.

As discussed above with respect to FIG. 1, embodiments of the invention can assist pharmaceutical manufacturers in retaining or shifting their market share for particular drugs. The operation of embodiments of the invention will now be described below with reference to FIGS. 2-6.

Operational Overview

Figure 2:
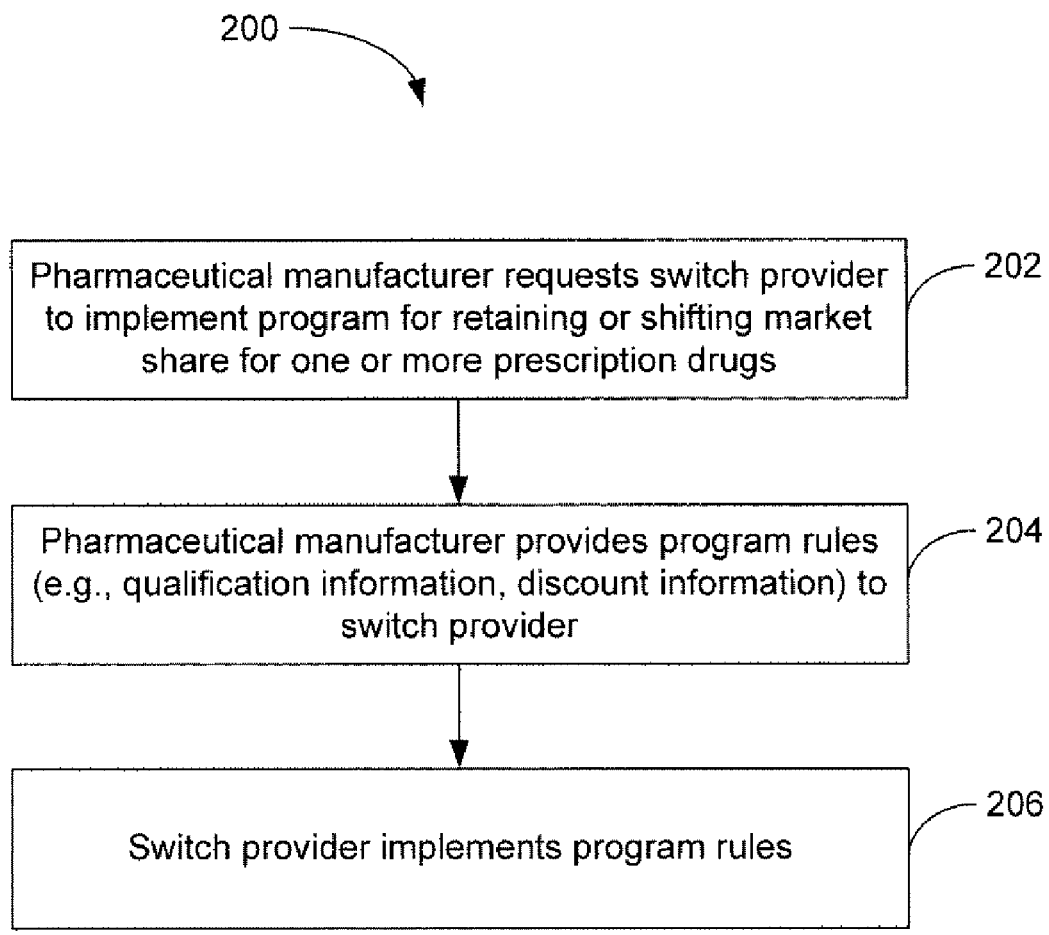
FIG. 2 provides an exemplary method by which pharmaceutical manufacturers can set up program rules with a switch provider to retain drug market share, according to an embodiment of the invention.

FIG. 2 illustrates a method 200 by which pharmaceutical manufacturers can set up program rules with a switch provider 104 in order to retain or shift their drug market share. Referring to FIG. 2, a pharmaceutical manufacturer may request that a switch provider 104 implement a program for retaining or shifting its market share for one or more drugs. According to an embodiment of the invention, this request may be an electronic request (e.g., e-mail, messaging, direct communications, etc.) over network 110 between the switch provider 104 and a pharmaceutical manufacturer computer (not shown). However, it will be appreciated that the request may also be made using facsimile, telephone, postal mail, and other electronic and non-electronic communication means known to one of ordinary skill in the art.

Still referring to FIG. 2, in block 204, the pharmaceutical manufacturer may provide program rules, which may include eligibility and/or discount information to the switch provider 104. This eligibility and/or discount information will be discussed below in accordance with the several illustrative embodiments. According to block 206, the switch provider 104 may then implement the program rules. It will be appreciated that these program rules may be modified and/or updated by the pharmaceutical manufacturer or the switch provider 104 from time to time. The implementation of the program rules by the switch provider 104 will now be described in further detail below with respect to several exemplary embodiments show in FIGS. 3-6.

Embodiment #1 (Market Share Retention Program ("MSRP"))

Figure 3A:
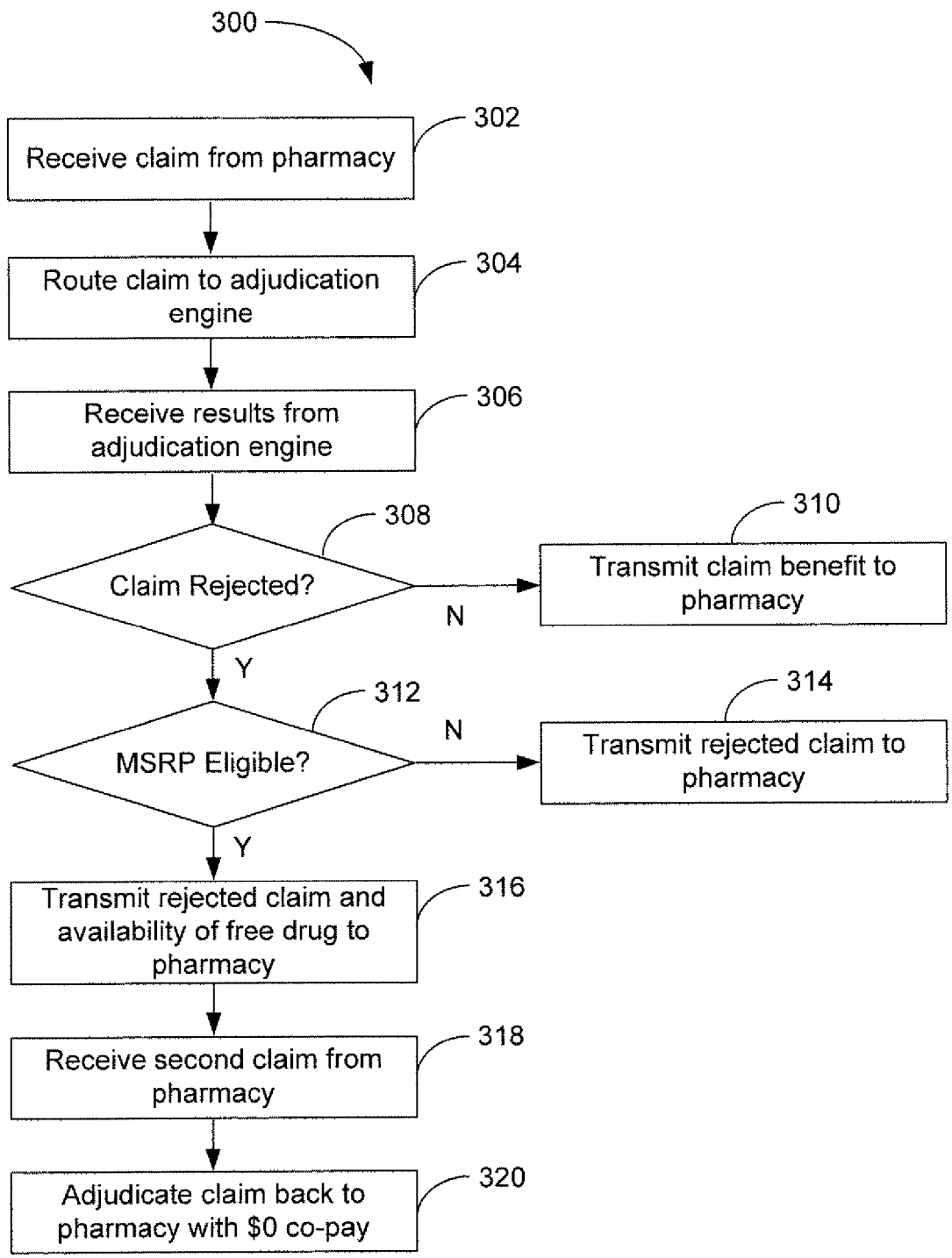
FIGS. 3-5 illustrate exemplary methods by which the switch provider may operate to retain or shift prescription market share for one or more pharmaceutical manufacturers, according to embodiments of the invention.

FIG. 3A illustrates an exemplary method 300 by which the switch provider 104 operates to retain or shift drug market share when a claim is rejected by a payor, according to an exemplary embodiment of the invention. In block 302, the switch provider 104 may receive the electronic claim submission from the pharmacy 102 computer via network 110 and I/O Interface 130. Generally, the customer 124 may provide a drug order that is entered by a pharmacy 102 employee into the pharmacy 102 computer, which is then transmitted to the switch provider 104 in the form of an electronic claim submission.

In block 304, the switch provider 104 may route the claim to an adjudication engine 108 for further processing (e.g., benefits and/or coverage determination processing) via network 110 and I/O interface 130. According to an embodiment of the invention, the Banking Identification Number (BIN)/ Processor Control Number (PCN) may specify which adjudication engine 108 the claim should be routed to. According to another embodiment of the invention, the switch provider 104 may also include a routing table, perhaps stored in memory 128 or data storage device 142, for determining which adjudication engine 108 the claim should be routed to. As described above, the adjudication engine 108 may be associated with a discount program or a third-party payor such as a PBM or insurance company.

In block 306, the switch provider 104 may receive the status or results of the benefits and/or coverage determination from the adjudication engine 108. If the drug is covered by the payor, then the switch provider 104 may receive the covered (e.g., insured) amount and the patient (e.g., customer 124) co-pay amount from the adjudication engine 108. However, if the drug is not covered by the payor, then the switch provider 104 may receive a rejected claim notice from the adjudication engine 108 (block 306).

Accordingly, if block 308 determines that the claim has not been rejected, then processing proceeds with block 310, where the claim benefit (e.g., covered and co-pay amounts) may be transmitted by the switch provider 104 to the pharmacy 102 computer via network 110 and respective I/O Interfaces 130, 114. In an alternative embodiment of the invention, block 310 may also include determining whether other discounts (e.g., vouchers, coupons, etc.) are available from the pharmaceutical manufacturer to reduce the customer 124 copay amounts, as illustrated and described below with respect to FIGS. 4-5.

On the other hand, block 308 may determine that the claim has been rejected by the adjudication engine 108. In this situation, processing may continue with block 312 determining whether the rejected claim may still be eligible for partial or full coverage or payment by the pharmaceutical manufacturer under an exemplary program having associated program rules and which may be referred to as the "MSRP" program. It will be appreciated that the pharmaceutical manufacturer may have incentives to cover the customer's 124 drug costs for a rejected claim (e.g., when seeking preferred status, inclusion in an insurance plan, or to sell complementary products, etc.).

Block 312, which will be described separately below, then determines whether the claim is eligible for coverage by the pharmaceutical manufacturer under the exemplary MSRP program. It will be appreciated that eligibility determination of block 312 may be determined, at least in part, prior to routing the claim to the adjudication engine in block 304. If the eligibility determination is performed prior to block 304, then the switch provider 104 may store the preliminary eligibility determination in a history table (e.g., stored in memory 128 or data storage device 142) for later retrieval.

If block 312 determines that the claim is not eligible for coverage by the pharmaceutical manufacturer, then the switch provider 104 transmits a rejected claim (e.g., not covered by a payor) to the pharmacy 102 computer. On the other hand, if block 312 determines that the claim is eligible for coverage by the pharmaceutical manufacturer, then processing may continue with block 316.

In block 316, the switch provider 104 may transmit the rejected claim to the pharmacy 102 computer along with a notice of availability of coverage (e.g., free drug) to the pharmacy 102 computer. This notice of availability of coverage and/or rejected claim information may also be stored in a history table of the switch provider 104 (e.g., in memory 128 or data storage device 142) for subsequent verification and reconciliation. According to an embodiment of the invention, block 316 may also include instructions to the pharmacy 102 computer to submit a second claim to obtain the free drug for the customer 124.

Accordingly, in block 318, the switch provider 104 may receive a second claim from the pharmacy 102 computer. In block 318, the switch provider 104 may also verify that a history record associated with the notice of availability of coverage and/or rejected claim exists in a history record of the switch provider 104 before proceeding to block 320, according to an embodiment of the invention. In block 320, the switch provider 104 adjudicates the second claim and notifies the pharmacy 102 computer that the second claim has been paid (e.g., with a customer 124 co-pay of $0). In this situation, the switch provider 104 may remit payment (e.g., Average Wholesale Price (AWP)–15%) to the pharmacy 102 on a periodic basis for the eligible MSRP program payments, and the switch provider 104 may receive reimbursement (e.g., AWP+10%) and/or processing fees from the pharmaceutical manufacturer.

It will be appreciated that variations of the method 300 are available without departing from embodiments of the invention. For example, according to an alternative embodiment of the invention, the switch provider 104 may automatically perform block 320 after determining that the claim is eligible for coverage under the MSRP program in block 312. Accordingly, the pharmacy 102 computer would not be required to receive a notice and submit a second claim (e.g., blocks 316 and 318) in order to receive coverage of the drug under the exemplary MSRP program. According to another alternative embodiment of the invention, the switch provider 104 may offer a printable coupon with the rejected claim in block 316. The pharmacy 102 computer may then print or otherwise redeem the printable coupon to obtain coverage under the exemplary MSRP program. With a printable coupon, the pharmacy 102 may receive payment for the coupon from the pharmaceutical manufacturer or through traditional coupon clearing houses. Furthermore, according to yet another alternative embodiment of the invention, under the MSRP program, the pharmaceutical manufacturer may only cover a portion of the drug costs, similar to what is described below with respect to FIGS. 4-5. Yet other variations are possible without departing from embodiments of the invention.

The eligibility of a claim for coverage under the MSRP program (block 312 of FIG. 3A) will now be discussed in further detail with respect to FIG. 3B. In particular, FIG. 3B begins with block 340 determining whether the claim is going to an excluded payor (and associated adjudication engine 108). The switch provider 104 may include a list of excluded BIN/PCN combinations for determining whether the claim is going to an excluded payor. Examples of excluded payors may include government payors or certain PBMs. If the claim is going to an excluded payor (block 340), then the switch provider 104 may determine that the claim is not MSRP eligible (block 342). In other words, the switch provider 102 may determine that coverage for the claim, and thus payment by the pharmaceutical manufacturer, is not available under the MSRP program (block 342).

Block 340 may also determine that the claim is not going to an excluded payor, in which case processing may continue with block 344 determining whether the patient (e.g., customer 124) is of the appropriate age. For example, if the MSRP program is directed towards young patients, then patients over 5 years of age may be excluded. Likewise, if the MSRP program is directed towards seniors, then patients under 65 years of age may be excluded. It will be appreciated that the appropriate ages may be varied without departing from embodiments of the invention. If block 344 determines that the patient is not of the appropriate age, then the switch provider 104 may determine that the claim is not MSRP eligible (block 342). However, if block 344 determines that the patient is of the appropriate age, then processing continues with block 346.

Block 346 may determine whether the pharmacy 102 submitting the claim is a participating provider in the MSRP program. According to an embodiment of the invention, the switch provider 104 may include a list of National Council for Prescription Drug Programs (NCPDP) numbers and/or national provider identifier (NPI) numbers for determining participating pharmacies 102. If block 346 determines the pharmacy 102 submitting the claim is a non-participating provider (block 346), then the switch provider 104 may determine that the claim is not MSRP eligible (block 342). On the other hand, block 346 may determine that the pharmacy 102 submitting the claim is a participating provider, and processing continues with block 348.

Block 348 determines whether the drug identified in the claim is eligible under the MSRP program. According to an embodiment of the invention, the switch provider 104 may compare the national drug code (NDC) specified by the claim to its list of eligible NDCs. In alternative embodiments, the switch provider 104 may also identify one or more classes or types of drugs as eligible under the MSRP program. If block 348 determines an ineligible drug, then the switch provider 104 may determine that the claim is not MSRP eligible (block 342). On the other hand, if block 348 determines an eligible drug, then processing continues with block 350.

Block 350 determines whether the claim was rejected by the payor for a qualified reason. According to an embodiment of the invention, some qualified reasons may include any of the following: (i) product not covered (e.g., NCPDP=70), (ii) refills not covered (e.g., NCPDP=73), and (iii) prior authorization required (e.g., NCPDP=75). Other qualified reasons may also be added or removed without departing from embodiments of the invention. If block 350 determines that the claim was not rejected for a qualified reason, then the switch provider 104 may determine that the claim is not MSRP eligible (block 342). On the other hand, if block 350 determines that the claim was rejected for a qualified reason, then processing proceeds to block 352. In block 352, the switch provider 104 determines that the claim is MSRP eligible. Accordingly, the rejected claim will be eligible for partial or full coverage by the pharmaceutical manufacturer.

Figure 3B:
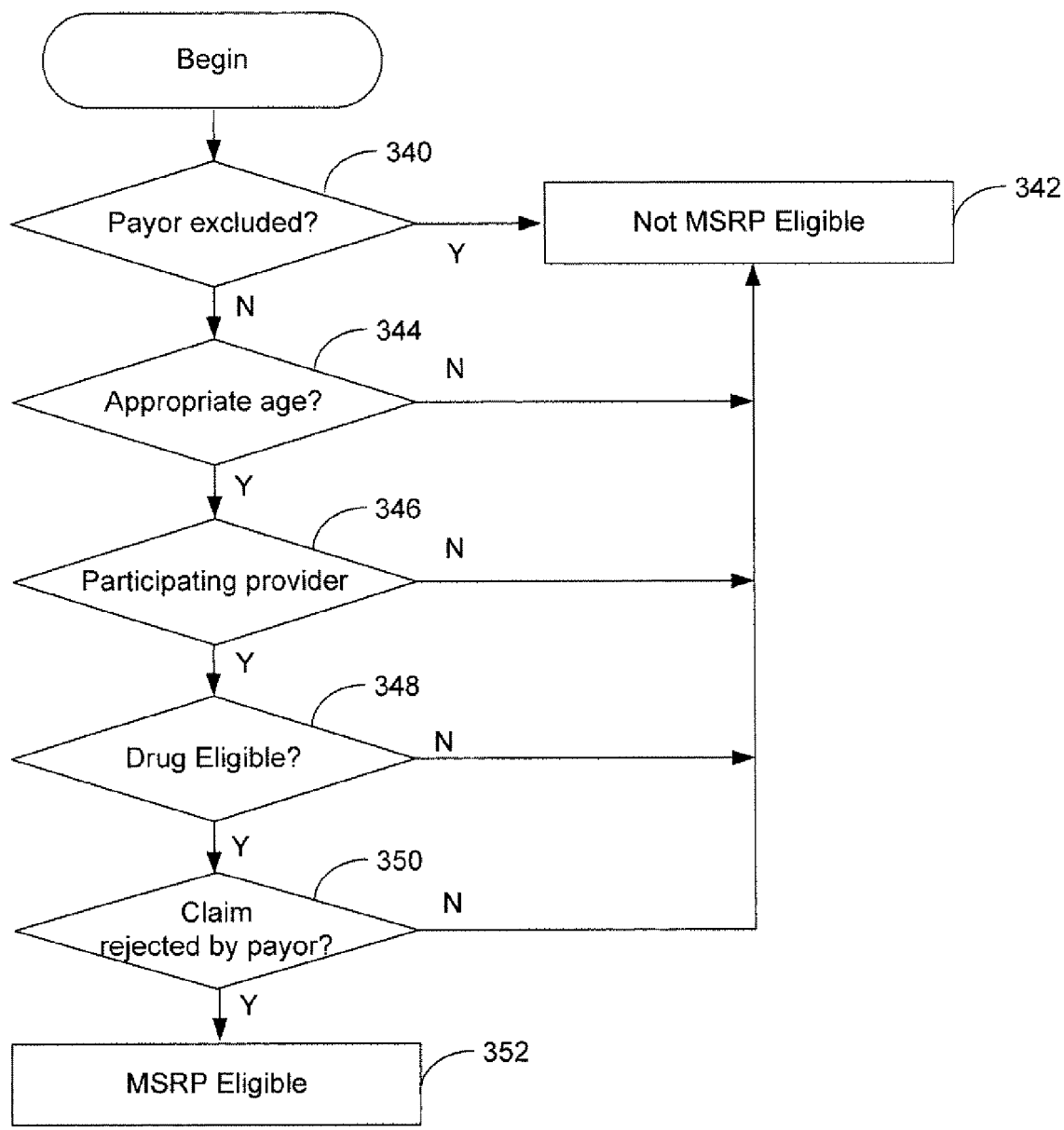

It will be appreciated that other conditions besides those illustrated in FIG. 3B may be utilized to determine MSRP eligibility without departing from embodiments of the invention. For example, MSRP eligibility may also be based, at least in part, upon the number of number of prescriptions filled by a patient in a particular amount of time or the length of time that the customer 124 has been using the drug.

EMBODIMENT #2 (eVoucher)

Figure 4A:
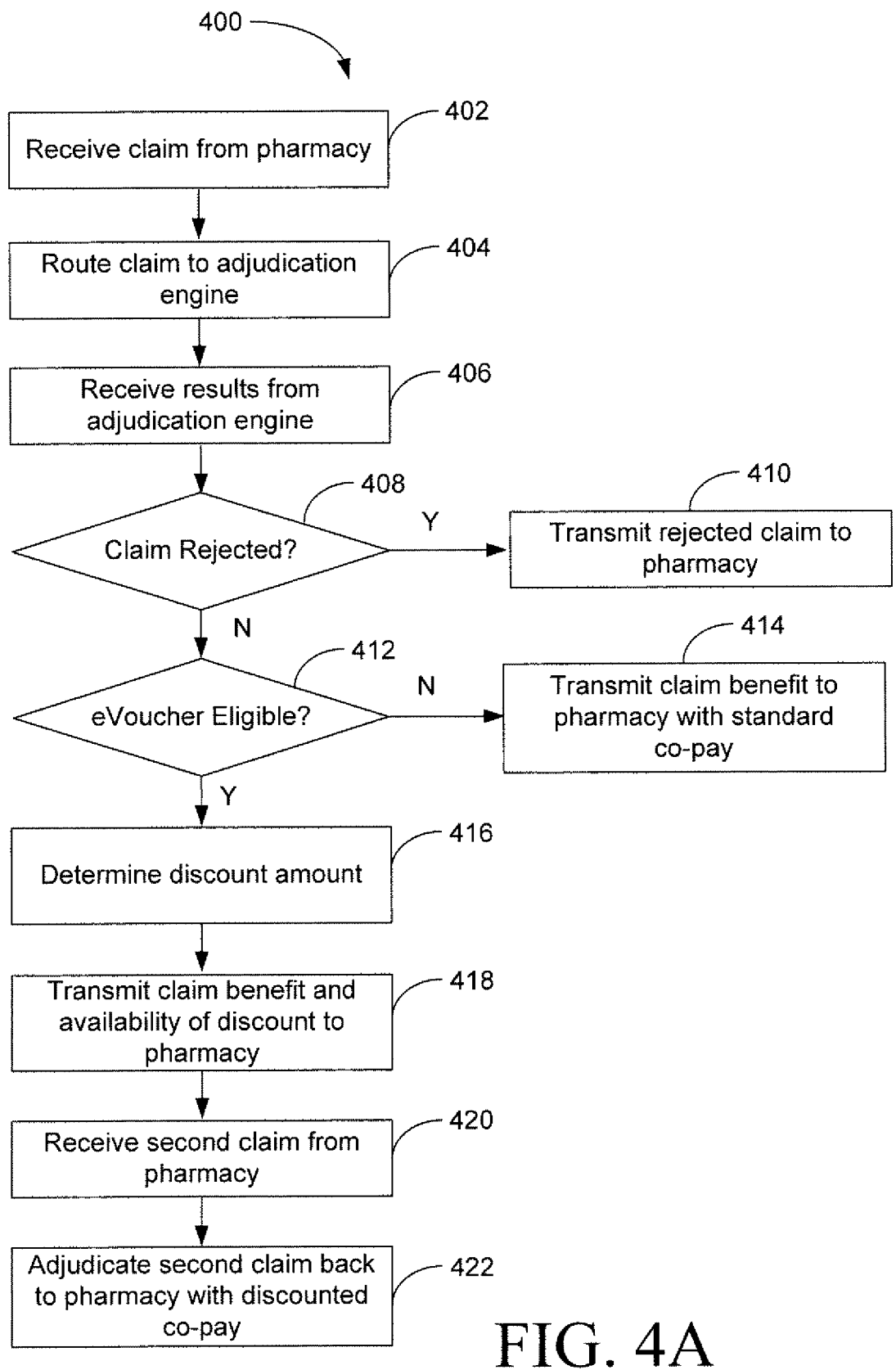

FIG. 4A illustrates an exemplary method 400 by which the switch provider 104 operates to retain or shift drug market share when a patient's co-pay exceeds a threshold amount, according to an exemplary embodiment of the invention. In block 402, the switch provider 104 may receive the electronic claim submission from the pharmacy 102 computer via network 110 and I/O Interface 130. Generally, the customer 124 may provide a drug order that is entered by a pharmacy 102 employee into the pharmacy 102 computer, which is then transmitted to the switch provider 104 in the form of an electronic claim submission.

In block 404, the switch provider 104 may route the claim to an adjudication engine 108 for further processing (e.g., benefits and/or coverage determination processing) via network 110 and I/O interface 130. According to an embodiment of the invention, the Banking Identification Number (BIN)/Processor Control Number (PCN) may specify which adjudication engine 108 the claim should be routed to. According to another embodiment of the invention, the switch provider 104 may also include a routing table, perhaps stored in memory 128 or data storage device 142, for determining which adjudication engine 108 the claim should be routed to. As described above, the adjudication engine 108 may be associated with a discount program or a third-party payor such as a PBM or insurance company.

In block 406, the switch provider 104 may receive the status or results of the benefits and/or coverage determination from the adjudication engine 108. If the drug is covered by the payor, then the switch provider 104 may receive the covered (e.g., insured) amount and the patient (e.g., customer 124) co-pay amount from the adjudication engine 108. However, if the drug is not covered by the payor, then the switch provider 104 may receive a rejected claim notice from the adjudication engine 108 (block 406).

Accordingly, if block 408 determines that the claim has been rejected, then processing proceeds with block 410, where the rejected claim is transmitted by the switch provider 104 to the pharmacy 102 computer via network 110 and respective I/O Interfaces 130, 114. On the other hand, block 408 may determine that the claim has been not been rejected by the adjudication engine 108. In this situation, processing may continue with block 412 determining whether the patient's co-pay amount may be reduced by a voucher, coupon, payment, or other discount provided by the pharmaceutical manufacturer under an exemplary program having associated program rules and which may be referred to as the "eVoucher" program. It will be appreciated that the pharmaceutical manufacturer may have incentives to reduce the patient's co-pay amount for a drug since patients may be a price sensitive group (e.g., willing to stop taking a drug or swap drugs based upon co-pay amounts).

Block 412, which will be described separately below, then determines whether the claim is eligible for coverage (e.g., voucher, coupon, payment, or other discount) by the pharmaceutical manufacturer under the exemplary eVoucher program. It will be appreciated that eligibility determination of block 412 may be determined, at least in part, prior to routing the claim to the adjudication engine in block 404. If the eligibility determination is performed prior to block 404, then the switch provider 104 may store the preliminary eligibility determination in a history table (e.g., stored in memory 128 or data storage device 142) for later retrieval.

If block 412 determines that the claim is not eligible for coverage by the pharmaceutical manufacturer, then the switch provider 104 transmits the claim benefit to the pharmacy 102 computer with the standard co-pay (e.g., non-discounted co-pay) received from the adjudication engine 108 in block 406 (block 414). On the other hand, if block 412 determines that the claim is eligible for coverage by the pharmaceutical manufacturer, then processing may continue with block 416.

In block 416, the eligible coverage or discount amount provided under the eVoucher program may be determined. According to an embodiment of the invention, the discount amounts may be percentage amounts, flat amounts, or variable amounts. Examples of determinations of coverage of discount amounts in block 416 will be provided in further detail below. Following block 416, processing proceeds to block 418.

In block 418, the switch provider 104 may transmit the claim benefit (e.g., insured amount and co-pay amount) to the pharmacy 102 computer along with a notice of availability of discount (e.g., specifying determined discount amount) to the pharmacy 102 computer. This notice of availability of discount may also be stored in a history table of the switch provider 104 (e.g., in memory 128 or data storage device 142) for subsequent retrieval, verification, and/or reconciliation. According to an embodiment of the invention, block 418 may also include transmitting instructions to the pharmacy 102 computer to submit a second claim (e.g., a coordination of benefits (COB) claim, a claim addressed to a particular BIN, etc.) to obtain the available discount for the customer 124.

Accordingly, in block 420, the switch provider 104 may receive a second claim from the pharmacy 102 computer. In block 420, the switch provider 104 may also verify that a history record associated with the determined discount exists in a history record of the switch provider 104 before proceeding to block 422, according to an embodiment of the invention. In block 422, the switch provider 104 adjudicates the second claim back to the pharmacy 102 computer with the discounted co-pay (e.g., the co-pay amount of block 406—determined discount amount of block 416). In this situation, the switch provider 104 may remit payment for the applied eVoucher discounts to the pharmacy 102 on a periodic basis, and the switch provider 104 may receive reimbursement and/or processing fees from the pharmaceutical manufacturer.

It will be appreciated that variations of the method 400 are available without departing from embodiments of the invention. According to another alternative embodiment of the invention, the switch provider 104 may offer a printable coupon with the transmitted claim benefit in block 414. The pharmacy 102 computer may then print or otherwise redeem the printable coupon to obtain coverage under the exemplary MSRP program. With a printable coupon, the pharmacy 102 may receive payment for the coupon from the pharmaceutical manufacturer or through traditional coupon clearing houses.

The various exemplary methods for determining the discount amounts under the eVoucher program will now be discussed according to three illustrative examples below. Discount Example #1: According to the first example, the program rules specify a minimum co-pay threshold (e.g., threshold T=$20) for the discount under the eVoucher to apply. In addition, the discount percent is a certain percentage (e.g., % Disc.=50%). A maximum discount limitation may apply (e.g., M=$25). In this example, the co-pay is the amount determined by the adjudication engine 108 in block 406.

a) Discount percent applies only to amount of co-pay above threshold: T=$20, % Disc=50%, Co-pay=$100, ∴ Disc. Amount=50%×($100−$20)=$40.

b) Discount percent applies only to amount of co-pay above threshold and maximum discount applies: T=$20, % Disc=50%, M=$25, Co-pay=$100, ∴ Disc. Amount=smaller (50%×($100−$20)=$40, $25)=$25.

c) Discount percent applies to entire co-pay amount: T=$20, % Disc=50%, Co-pay=$100, ∴ Disc. Amount=50%×($100)=$50.

d) Discount percent applies to entire co-pay amount and maximum discount applies: T=$20, % Disc=50%, M=$25, Co-pay=$100, ∴ Disc. Amount=smaller (50%×($100)=$50, $25)=$25.

Discount Example #2: According to the second example, the program rules specify a minimum co-pay threshold amount (e.g., threshold T=$20) for the discount under the eVoucher to apply. In addition, the discount amount is a flat discount amount (e.g., FD=$30). A limitation of a $0.00 (Limit=$0.00) applies so that the co-pay cannot be reduced below $0.00. In this example, the co-pay is the amount determined by the adjudication engine 108 in block 406.

a) Co-pay exceeds threshold and limitation does not apply: T=$20, FD=$30, Co-pay=$100, Limit=$0.00, ∴ Disc. Amount=$30.

b) Co-pay exceeds threshold and limitation applies: T=$20, FD=$30, Co-pay=$25, Limit=$0.00, ∴ Disc. Amount=$25.

c) Zero threshold: T=$0, FD=$30, co-pay=$X, limit=$0.00 ∴ If $X≧$30, then Disc. Amount=$30, else Disc. Amount=$X.

d) Co-pay does not exceed threshold: T=$20, FD=$30, co-pay=$10, ∴ Disc. Amount=$0.00.

Discount Example #3: According to the third example, the program rules specify a minimum co-pay threshold amount (e.g., threshold T=$20) for the discount under the eVoucher to apply. In addition, for co-pays exceeding the threshold amount, the discount amount is a variable amount to attempt to maintain a constant co-pay amount (here, $20). However, a maximum discount limitation may apply (e.g., M=$30). In this example, the co-pay is the amount determined by the adjudication engine 108 in block 406.

a) T=$20, M=$30, co-pay=$10, ∴ Disc. Amount=$0.00
  b) T=$20, M=$30, co-pay=$30, ∴ Disc. Amount=$10.00
  c) T=$20, M=$30, co-pay=$50, ∴ Disc. Amount=$30.00
  d) T=$20, M=unlimited, co-pay=$10, ∴ Disc. Amount=$0.00
  e) T=$20, M=unlimited, co-pay=$30, ∴ Disc. Amount=$10.00
  f) T=$20, M=unlimited, co-pay=$100, ∴ Disc. Amount=$80.00

The eligibility of a claim for coverage under the eVoucher program (block 412 of FIG. 4A) will now be discussed in further detail with respect to FIG. 4B. In particular, FIG. 4B begins with block 440 determining whether the claim is going to an excluded payor (and associated adjudication engine 108). The switch provider 104 may include a list of excluded BIN/PCN combinations for determining whether the claim is going to an excluded payor. Examples of excluded payors may include government payors or certain PBMs. If the claim is going to an excluded payor (block 440), then the switch provider 104 may determine that the claim is not eVoucher eligible (block 442). In other words, the switch provider 102 may determine that a voucher, coupon, payment, or other discount from the pharmaceutical provider is not available under the eVoucher program (block 442).

Block 440 may also determine that the claim is not going to an excluded payor, in which case processing may continue with block 444 determining whether the patient (e.g., customer 124) is of the appropriate age. For example, if the eVoucher program is directed towards young patients, then patients over 5 years of age may be excluded. Likewise, if the eVoucher program is directed towards seniors, then patients under 65 years of age may be excluded. It will be appreciated that the appropriate ages may be varied without departing from embodiments of the invention. If block 444 determines that the patient is not of the appropriate age, then the switch provider 104 may determine that the claim is not eVoucher eligible (block 442). However, if block 444 determines that the patient is of the appropriate age, then processing continues with block 446.

Block 446 may determine whether the pharmacy 102 submitting the claim is a participating provider in the eVoucher program. According to an embodiment of the invention, the switch provider 104 may include a list of National Council for Prescription Drug Programs (NCPDP) numbers and/or national provider identifier API) numbers for determining participating pharmacies 102. If block 446 determines the pharmacy 102 submitting the claim is a non-participating provider (block 446), then the switch provider 104 may determine that the claim is not eVoucher eligible (block 442). On the other hand, block 446 may determine that the pharmacy 102 submitting the claim is a participating provider, and processing continues with block 448.

Block 448 determines whether the drug identified in the claim is eligible under the eVoucher program. According to an embodiment of the invention, the switch provider 104 may compare the national drug code (NDC) specified by the claim to its list of eligible NDCs. In alternative embodiments, the switch provider 104 may also identify one or more classes or types of drugs as eligible under the eVoucher program. If block 448 determines an ineligible drug, then the switch provider 104 may determine that the claim is not eVoucher eligible (block 442). On the other hand, if block 448 determines an eligible drug, then processing continues with block 450.

Block 450 determines whether the co-pay is greater than a threshold amount. For example, the pharmaceutical manufacturer may indicate that only co-pays amounts that exceed a predetermined threshold amount (e.g., T=$20) should be considered for the voucher, coupon, payment, or discount under the eVoucher program. If block 450 determines that the co-pay is not greater than the threshold amount, then the claim may not be eVoucher eligible (block 442). On the other hand, if block 450 determines that the co-pay is greater than the threshold, then the switch provider 104 may determine that the claim is eVoucher eligible. Accordingly, the customer's 124 co-pay amount will be eligible for reduction via the voucher, coupon, discount, or other payment funded by the pharmaceutical manufacturer.

Figure 4B:
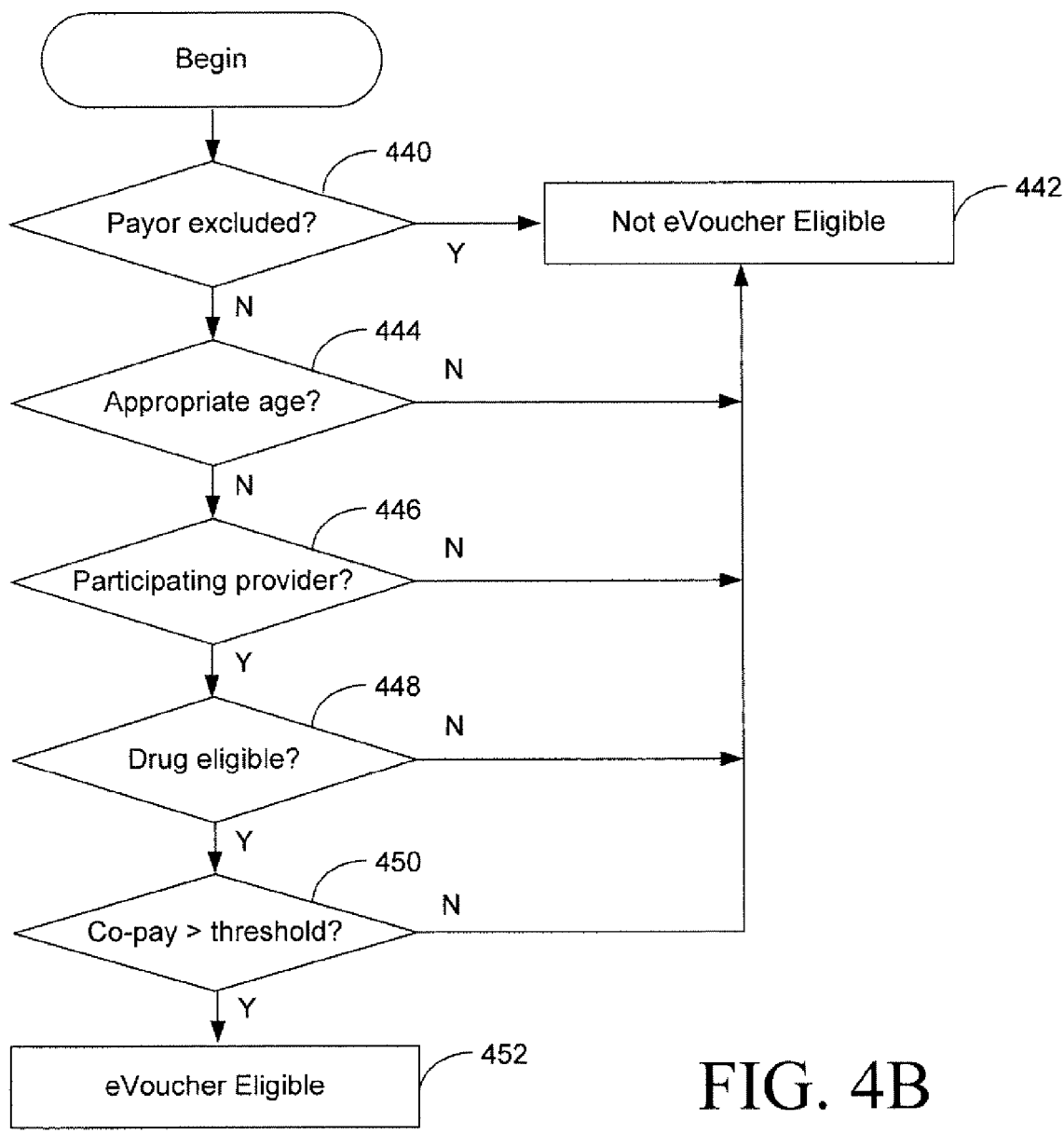

It will be appreciated that other conditions besides those illustrated in FIG. 4B may be utilized to determine MSRP eligibility without departing from embodiments of the invention. For example, MSRP eligibility may also be based, at least in part, upon the number of number of prescriptions filled by a patient in a particular amount of time or the length of time that the customer 124 has been using the drug.

Embodiment #3 (eVoucher Express)

Figure 5A:
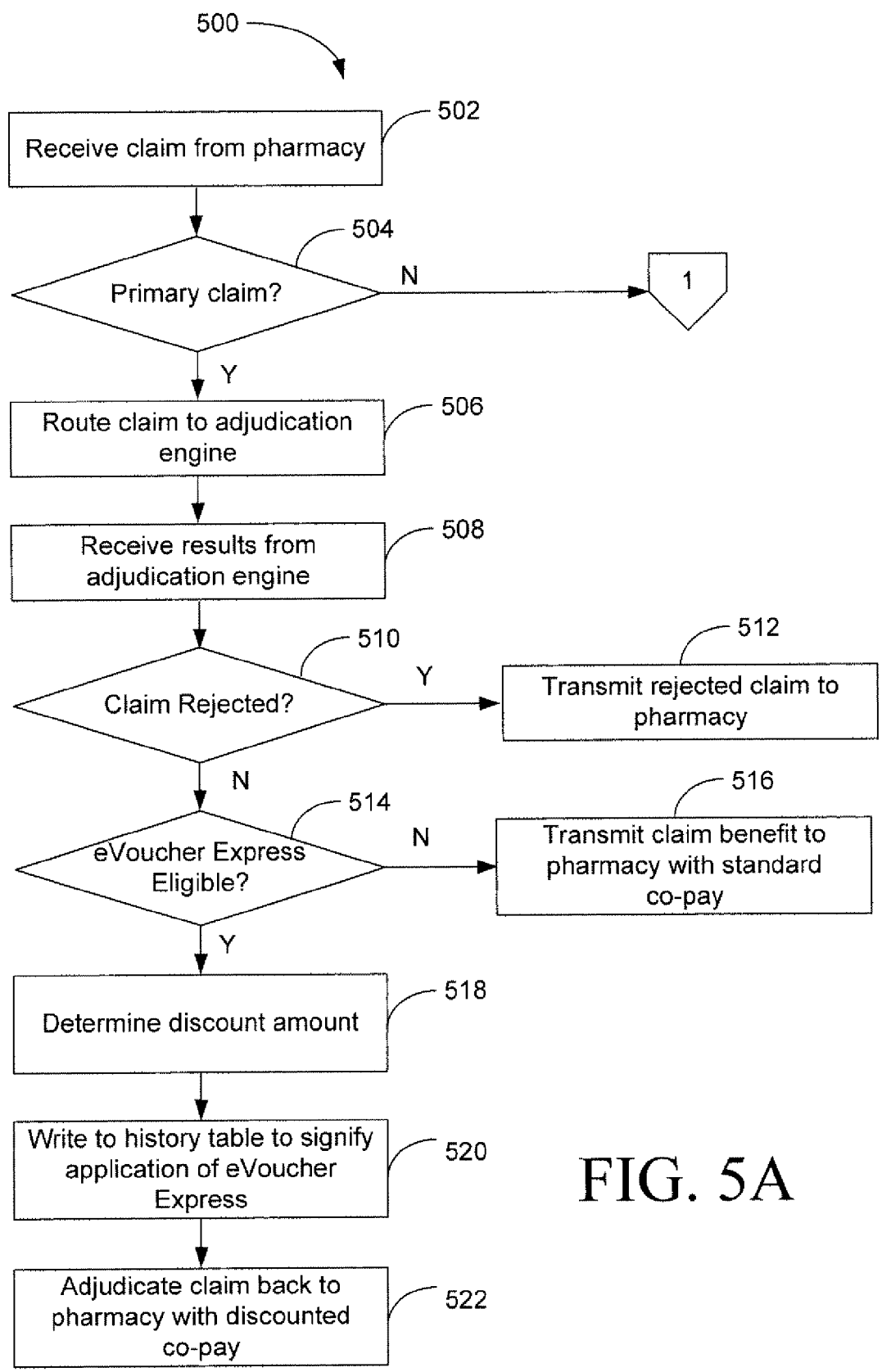

FIG. 5A illustrates an exemplary method 500 by which the switch provider 104 operates to retain or shift drug market share when a patient's co-pay exceeds a threshold amount, according to an exemplary embodiment of the invention. In block 502, the switch provider 104 may receive the electronic claim submission from the pharmacy 102 computer via network 110 and I/O Interface 130. Generally, the customer 124 may provide a drug order that is entered by a pharmacy 102 employee into the pharmacy 102 computer, which is then transmitted to the switch provider 104 in the form of an electronic claim submission.

In block 504, the switch provider determines whether the received claim is a primary claim. According to an embodiment of the invention, a primary claim may be determined by examining the other coverage code (OCC) in the received claim. Therefore, a primary claim may have an OCC=1, a secondary claim may have an OCC=2, a tertiary claim may have an OCC=3, and the like. The handling of non-primary claims identified in block 504 will be discussed below with respect to FIG. 5B. On the other hand, if block 504 determines that the received claim is a primary claim (e.g., OCC=1), then processing proceeds to block 506.

In block 506, the switch provider 104 may route the claim to an adjudication engine 108 for further processing (e.g., benefits and/or coverage determination processing) via network 110 and I/O interface 130. According to an embodiment of the invention, the Banking Identification Number (BIN)/Processor Control Number (PCN) may specify which adjudication engine 108 the claim should be routed to. According to another embodiment of the invention, the switch provider 104 may also include a routing table, perhaps stored in memory 128 or data storage device 142, for determining which adjudication engine 108 the claim should be routed to. As described above, the adjudication engine 108 may be associated with a discount program or a third-party payor such as a PBM or insurance company.

In block 508, the switch provider 104 may receive the status or results of the benefits and/or coverage determination from the adjudication engine 108. If the drug is covered by the payor, then the switch provider 104 may receive the covered (e.g., insured) amount and the patient (e.g., customer 124) co-pay amount from the adjudication engine 108. However, if the drug is not covered by the payor, then the switch provider may receive a rejected claim notice from the adjudication engine 108 (block 508).

Accordingly, if block 510 determines that the claim has been rejected, then processing proceeds with block 512, where the rejected claim is transmitted by the switch provider 104 to the pharmacy 102 computer via network 110 and respective I/O Interfaces 130, 114. On the other hand, block 510 may determine that the claim has been not been rejected by the adjudication engine 108. In this situation, processing may continue with block 514 determining whether the patient's co-pay amount may be reduced by a voucher, coupon, payment, or other discount provided by the pharmaceutical manufacturer under an exemplary program having associated program rules and which may be referred to as the "eVoucher Express" program. It will be appreciated that the pharmaceutical manufacturer may have incentives to reduce the patient's co-pay amount for a drug since patients may be a price sensitive group (e.g., willing to stop taking a drug or swap drugs based upon co-pay amounts).

Block 514, which will be described separately below with respect to FIG. 5C, then determines whether the claim is eligible for coverage (e.g., voucher, coupon, payment, or other discount) by the pharmaceutical manufacturer under the exemplary eVoucher Express program. It will be appreciated that eligibility determination of block 514 may be determined, at least in part, prior to routing the claim to the adjudication engine in block 504. If the eligibility determination is performed prior to block 504, then the switch provider 104 may store the preliminary eligibility determination in a history table (e.g., stored in memory 128 or data storage device 142) for later retrieval.

If block 514 determines that the claim is not eligible for coverage by the pharmaceutical manufacturer, then the switch provider 104 transmits the claim benefit to the pharmacy 102 computer with the standard co-pay (e.g., non-discounted co-pay) received from the adjudication engine 108 in block 508 (block 516). On the other hand, if block 514 determines that the claim is eligible for coverage by the pharmaceutical manufacturer, then processing may continue with block 518.

In block 518, the eligible coverage or discount amount provided under the eVoucher program may be determined. According to an embodiment of the invention, the discount amounts may be percentage amounts, flat amounts, or variable amounts, as described above. Following block 518, processing proceeds to block 520.

In block 520, the switch provider 104 may write to its history table (e.g., stored in memory 128 and data storage device 142) to indicate that the determined discount amount under the eVoucher Express program is to be applied for the instant claim (block 520). Accordingly, in block 522, the switch provider 104 adjudicates the instant claim back to the pharmacy 102 computer with the discounted co-pay (e.g., the co-pay amount of block 508—determined discount amount of block 518). In this situation, the switch provider 104 may remit payment for the applied eVoucher Express discounts to the pharmacy 102 on a periodic basis, and the switch provider 104 may receive reimbursement and/or processing fees from the pharmaceutical manufacturer.

Figure 5B:
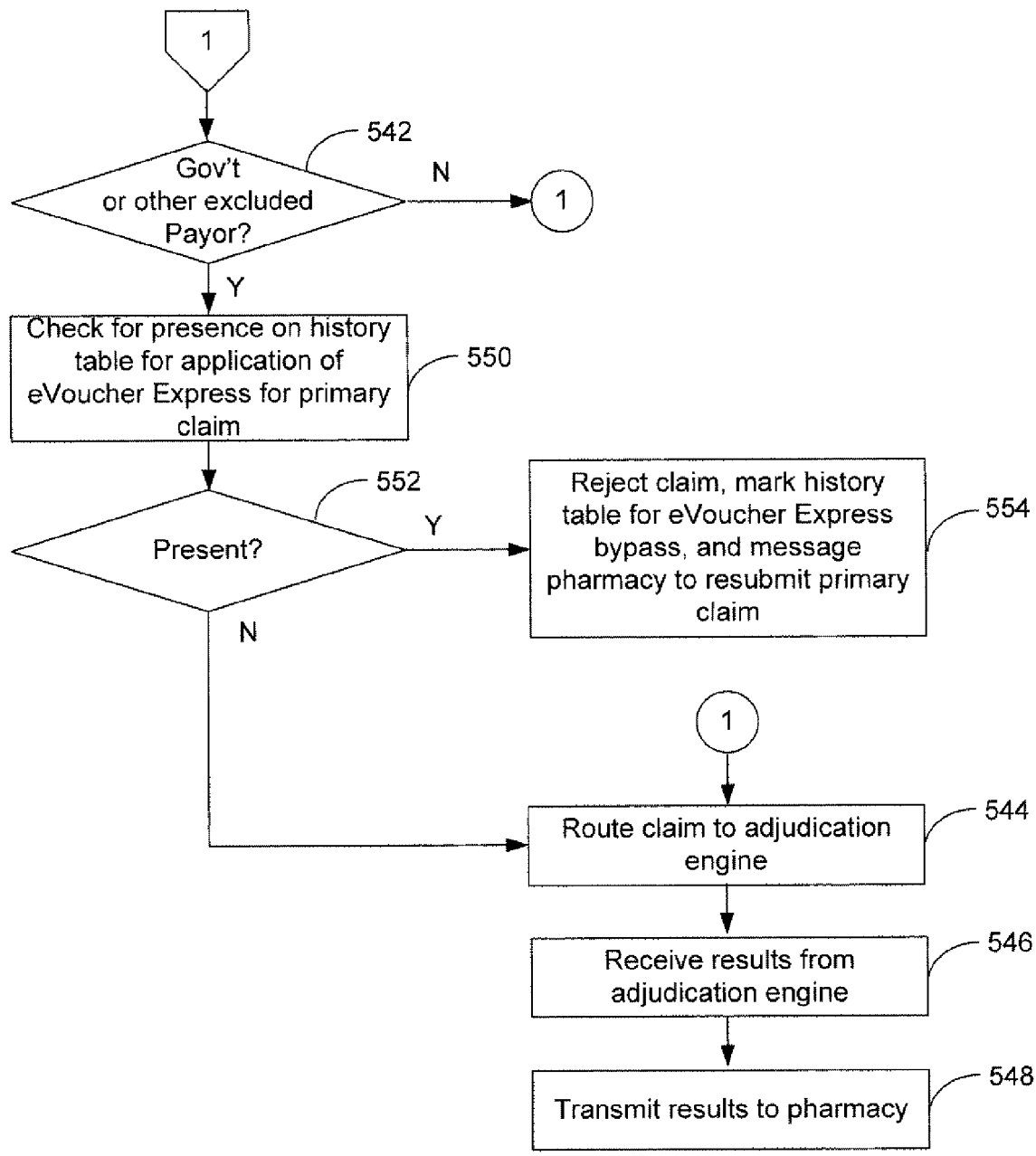

FIG. 5B illustrates an exemplary flow diagram for handling the situation where a non-primary claim is received by the switch provider 104. In particular, primary claims are typically paid by one or more third-party payors, described above, while secondary claims may be submitted to a government payor for the remaining amount. As government payors are typically payors of last resort, the government payors require the switch provider 104 to specifically identify all payments made at point of sale (POS). However, according to an embodiment of the invention, one or more of the vouchers, coupons payments, or other discounts provided with the primary claim under the eVoucher Express program may not expressly be included or identified at the time the transaction is completed at the POS. Accordingly, it may be necessary to intercept associated secondary claims submitted to a government payor and determine whether any vouchers, coupons, payments, or other discounts have been invoked under the eVoucher Express program on the primary claim. If the primary claim includes the vouchers, coupons, payments, or other discounts, it may be necessary to reverse the primary claim and resubmit the primary claim without invoking the vouchers, coupons payments, or other discounts under the eVoucher Express program.

FIG. 5B thus illustrates a method of intercepting a secondary claim submitted to a government payor to determine whether any vouchers, coupons, payments, or other discounts have been invoked on the primary claim under the eVoucher Express program. In block 542 of FIG. 5B, the switch provider 104 may determine whether a government payor or other excluded payor is identified as the destination of the non-primary claim (e.g., a secondary claim, tertiary claim, etc.). According to an embodiment of the invention, the switch provider 104 may make this determination based upon the BIN/PCN identified in the destination of the received non-primary claim. If block 542 determines that there is no government payor or excluded payor identified in the destination of the received claim, then processing continues to blocks 544 (switch provider 104 route claim to adjudication engine 108), 546 (switch provider 104 receives results from adjudication engine 108), and 548 (switch provider 104 transmits results (e.g., covered amount and co-pay amount) to pharmacy 102 computer).

On the other hand, the switch provider 104 may determine in block 542 that a government payor or excluded payor is identified in the destination of the received claim. Processing would then proceed with the switch provider 104 examining its history table for the application on of a voucher, coupon, payment, or other discount under the eVoucher Express program for the associated primary claim (block 550). If the history table does not indicate the application of the voucher, coupon, payment, or other discount under the eVoucher Express program for the primary claim (block 552), then processing proceeds with blocks 544, 546, and 548, described previously. On the other hand, if the history table does indicate the application of the voucher, coupon, payment, or other discount under the eVoucher Express program for the primary claim, then processing continues with block 554. In block 554, the switch provider 104 rejects the received non-primary claim (e.g., secondary claim), marks the history table for eVoucher Express bypass, and messages the pharmacy 102 computer to resubmit the primary claim. As will be discussed with respect to the eVoucher Express eligibility determination of block 514, the marking of the eVoucher Express bypass will result in the resubmitted primary claim not being eVoucher Express eligible.

The eligibility of a claim for coverage under the eVoucher Express program (block 514 of FIG. 5A) will now be discussed in further detail with respect to FIG. 5C. In particular, FIG. 5C begins with block 580 determining whether the eVoucher Express bypass has been set in the history table. If so, then the claim is not eVoucher Express eligible (block 584), and the system 500 will not apply any vouchers, coupons, payments, or other discounts to the received claim. However, if the eVoucher Express bypass has not been set, then processing proceeds to block 582.

Block 582 determines whether the claim is going to an excluded payor (and associated adjudication engine 108). The switch provider 104 may include a list of excluded BIN/PCN combinations for determining whether the claim is going to an excluded payor. Examples of excluded payors may include government payors or certain PBMs. If the claim is going to an excluded payor (block 582), then the switch provider 104 may determine that the claim is not eVoucher Express eligible (block 584). In other words, the switch provider 102 may determine that a voucher, coupon, payment, or other discount from the pharmaceutical provider is not available under the eVoucher Express program (block 584).

Block 582 may also determine that the claim is not going to an excluded payor, in which case processing may continue with block 586 determining whether the patient (e.g., customer 124) is of the appropriate age. For example, if the eVoucher Express program is directed towards young patients, then patients over 5 years of age may be excluded. Likewise, if the eVoucher Express program is directed towards seniors, then patients under 65 years of age may be excluded. It will be appreciated that the appropriate ages may be varied without departing from embodiments of the invention. If block 586 determines that the patient is not of the appropriate age, then the switch provider 104 may determine that the claim is not eVoucher Express eligible (block 584). However, if block 586 determines that the patient is of the appropriate age, then processing continues with block 588.

Block 588 may determine whether the pharmacy 102 submitting the claim is a participating provider in the eVoucher Express program. According to an embodiment of the invention, the switch provider 104 may include a list of National Council for Prescription Drug Programs (NCPDP) numbers and/or national provider identifier (NPI) numbers for determining participating pharmacies 102. If block 558 determines the pharmacy 102 submitting the claim is a non-participating provider, then the switch provider 104 may determine that the claim is not eVoucher Express eligible (block 584). On the other hand, block 588 may determine that the pharmacy 102 submitting the claim is a participating provider, and processing continues with block 590.

Block 590 determines whether the drug identified in the claim is eligible under the eVoucher Express program. According to an embodiment of the invention, the switch provider 104 may compare the national drug code (NDC) specified by the claim to its list of eligible NDCs. In alternative embodiments, the switch provider 104 may also identify one or more classes or types of drugs as eligible under the eVoucher Express program. If block 590 determines an ineligible drug, then the switch provider 104 may determine that the claim is not eVoucher eligible (block 584). On the other hand, if block 590 determines an eligible drug, then processing continues with block 592.

Block 592 determines whether the co-pay is greater than a threshold amount. For example, the pharmaceutical manufacturer may indicate that only co-pays amounts that exceed a predetermined threshold amount (e.g., T=$20) should be considered for the voucher, coupon, payment, or discount under the eVoucher Express program. If block 592 determines that the co-pay is not greater than the threshold amount, then the claim may not be eVoucher Express eligible (block 584). On the other hand, if block 592 determines that the co-pay is greater than the threshold, then the switch provider 104 may determine that the claim is eVoucher Express eligible. Accordingly, the customer's 124 co-pay amount will be eligible for reduction via the voucher, coupon, discount, or other payment funded by the pharmaceutical manufacturer.

Figure 5C:
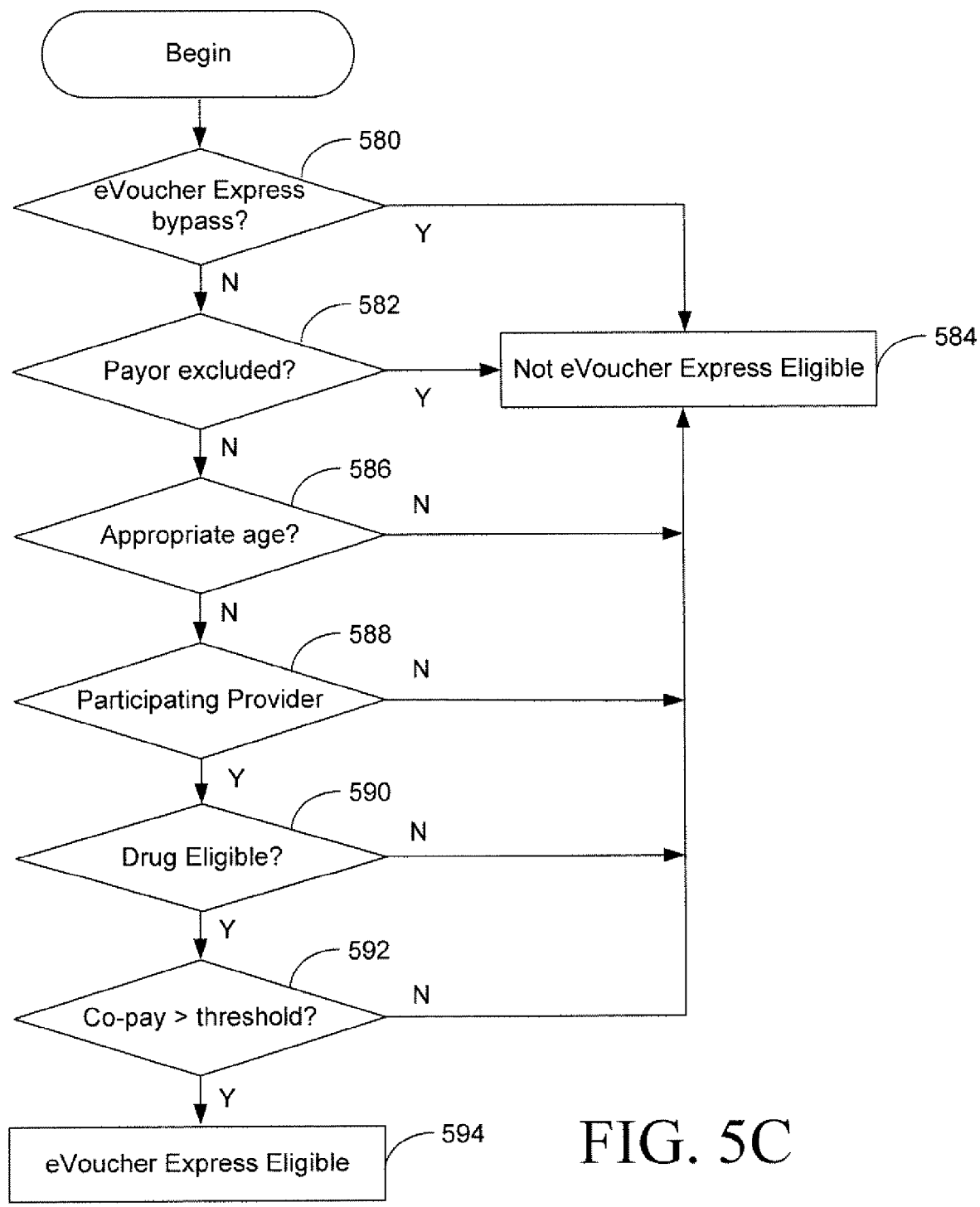

It will be appreciated that other conditions besides those illustrated in FIG. 5C may be utilized to determine eVoucher Express eligibility without departing from embodiments of the invention. For example, eVoucher Express eligibility may also be based, at least in part, upon the number of number of prescriptions filled by a patient in a particular amount of time or the length of time that the customer 124 has been using the drug.

It will also be appreciated that while the eligibility rules for the MSRP, eVoucher, and eVoucher Express programs have been discussed individually, they may also be combined into a single set of eligibility rules. With a single set of eligibility rules, the switch provider may determine whether the pharmacy 102 is a participating provider and if so, determine the appropriate MSRP, eVoucher, or eVoucher Express rules to utilize. Other variations will be appreciated by those of ordinary skill in the art.

Reversal of Discount Transactions

In accordance with an embodiment of the invention, there are some instances where the pharmaceutical manufacturer may be credited where a previously submitted claim is returned or reversed. Such returns or reversals may be necessary where, as described above, a government payor is involved in a secondary claim, and the pharmaceutical manufacturer provided a coupon, voucher, payment, or other discount with a primary claim. Such returns or reversals may also be necessary where an eligible customer 124 does not pick up the drug or otherwise returns the drug where the pharmaceutical manufacturer provided a coupon, voucher, payment, or other discount. In these situations, the pharmaceutical manufacturer may need to be credited with such a return.

Figure 6:
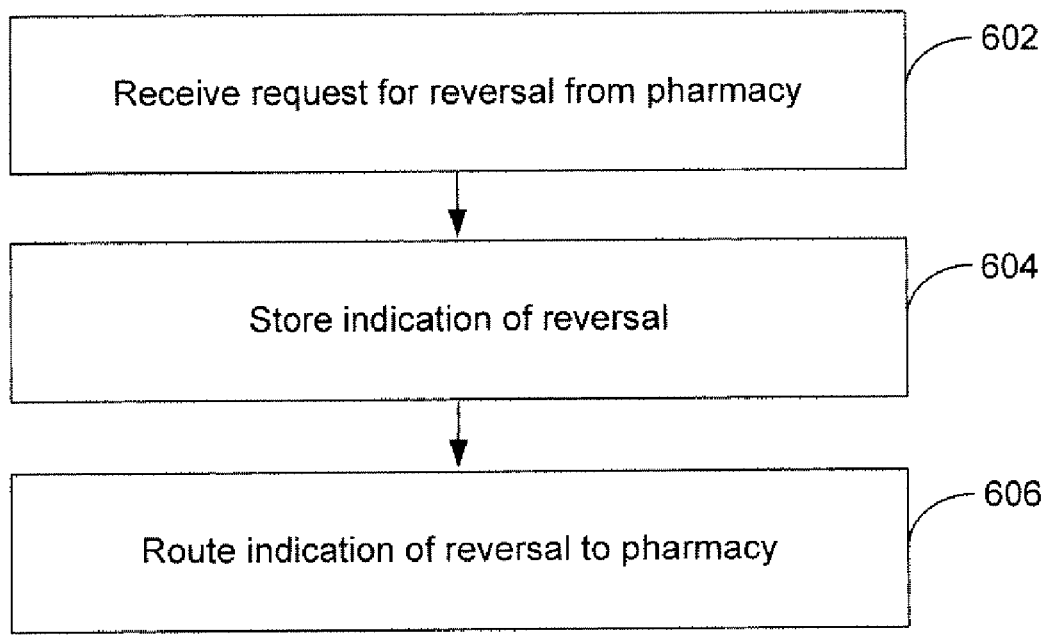
FIG. 6 illustrates an exemplary method for crediting a pharmaceutical manufacturer with returns or reversals, according to exemplary embodiments of the invention.

FIG. 6 illustrates an exemplary method for crediting a pharmaceutical manufacturer with returns or reversals. Referring to FIG. 6, the pharmacy 102 computer may submit a request for reversal (e.g., a B2 transaction) that may include a BIN to the switch provider 104 (block 602). The request for reversal may include information identifying the claim in which the pharmaceutical manufacturer agreed to provide a coupon, voucher, payment, or other discount. As shown in block 602, based on the request for reversal, the switch provider 104 would locate the previously stored indication (e.g., a history record) for the identified claim and reverse the indication such that the claim is now considered returned or unpaid, as indicated by block 604. The switch provider 104 then routes an indication of the successful reversal back to pharmacy 102 computer (block 606).

Pharmacy Payments for Coupons, Vouchers, Payments, or Other Discounts

As described above, one or more vouchers, coupons, payments, or other discounts may be provided for claim submissions associated with eligible customers 124. These coupons, vouchers, payments, or other discounts may be ultimately funded by the pharmaceutical manufacturers. As described above, the switch provider 104 may provide periodic payments to one or more pharmacies 102, and the switch provider 104 may be reimbursed (including any transaction or processing fees) for such payments by the pharmaceutical manufacturer.

However, when the switch provider 104 applies a voucher, coupon payment, or other discount to a claim submission, as described above, the information associated with the paid claim may not account for the amount of the coupon, voucher, payment, or other discount. Accordingly, when the pharmacy 102 accounts for the transactions on its books, the total amount receivable may be deficient.

According to an embodiment of the invention, the switch provider 104 may provide a reconciliation report to assist the pharmacy 102 with accounting for the deficiency associated with the applied coupons, vouchers, payments, or other discounts funded by the pharmaceutical manufacturer. The reports may be provided electronically via network 110 or through another communications means such as facsimile, postal mail, and the like. Each report may summarize transactions for a particular time period (e.g., a day, a week, etc.). Exemplary information included on the reports include for each transaction, the one or more of the associated pharmacy 102, the prescription number, the date of service, the drug (e.g., NDC), quantity, co-pay amount, and the amount of the applicable coupons, vouchers, payments, or other discounts. The report may also include the final customer out-of-pocket amount as well as an administrative fee payable from the switch provider 104 to the pharmacy 102.

According to another embodiment of the invention, the switch provider 104 may also provide a specific transaction type (e.g., based upon a particular BIN/PCN) by which the pharmacy 102 may request payment from the switch provider 104 in accordance with the reports provided by the switch provider 104. In particular, the pharmacy 102 computer may transmit a claim submission to the switch provider 104, where the claim submission includes the accumulated payment amount from the report that is due to the pharmacy 102. In other words, this claim submission may request, in a single claim submission, payment for all transactions listed in the received report. The claim submission may be associated with a specific transaction (e.g., BIN/PCN) and further specify the identity of the pharmacy 102, a dummy drug identifier (e.g., NDC), and a date of service. The switch provider 104 may then receive the claim submission, arrange for payment to the pharmacy 102, and transmit an indication of such payment or payable to the pharmacy 102 computer.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method of retaining or shifting prescription market share, comprising:
   receiving an insurance claim from a pharmacy computer, wherein the insurance claim is for a drug requested by a customer;
   routing the insurance claim to an adjudication engine for insurance benefits processing;
   receiving, from the adjudication engine, insurance coverage information for the insurance claim, wherein the insurance coverage information indicates an amount payable by an insurance plan and an amount payable by the customer;
   determining that a discount is available to reduce the amount payable by the customer, wherein the discount is funded by a pharmaceutical entity, wherein an amount of the discount is based at least in part on the amount payable by the customer; and
   transmitting at least a notice of availability of the discount to the pharmacy computer,
   wherein the prior steps are performed by one or more computers.

2. The computer-implemented method of claim 1, wherein determining that the discount is available includes determining one of: (i) whether the insurance claim is rejected by a payor for the insurance plan based at least in part on the received coverage information or (ii) whether the amount payable by the customer exceeds a threshold.

3. The computer-implemented method of claim 1, wherein determining that the discount is available includes determining at least one of: (i) whether a payor for the insurance plan is excluded, (ii) whether the customer is of the appropriate age, (iii) whether the pharmacy computer is associated with a participating provider, or (iv) whether the drug is included on an eligible list of drugs.

4. The computer-implemented method of claim 1, wherein the discount is a percentage discount, a flat discount amount, or a variable discount amount.

5. The computer-implemented method of claim 4, wherein the discount is a variable discount amount that enables a specification of a maximum customer amount payable for the drug.

6. The computer-implemented method of claim 1, wherein transmitting at least a notice of availability of the discount to the pharmacy computer includes transmitting at least a portion of the coverage information for the claim.

7. A system for retaining or shifting prescription market share, comprising:
   a memory configured to store computer-executable instructions;
   a processor in communication with the memory, wherein the processor is configured to execute the computer-executable instructions to:
      receive an insurance claim from a pharmacy computer, wherein the insurance claim is for a drug requested by a customer;
      route the insurance claim to an adjudication engine for benefits processing;
      receive, from the adjudication engine, insurance coverage information for the claim, wherein the coverage information indicates an amount payable by an insurance plan and an amount payable by the customer;
      determine that a discount is available to reduce the amount payable by the customer, wherein the discount funded by a pharmaceutical entity, wherein an amount of the discount is based at least in part on the amount payable by the customer; and
      transmit at least a notice of availability of the discount to the pharmacy computer.

8. The system of claim 7, wherein the processor is configured to determine that the discount is available by determining one of: (i) whether the insurance claim is rejected by a payor for the insurance plan based at least in part on the received coverage information or (ii) whether the amount payable by the customer exceeds a threshold.

9. The system of claim 7, wherein the processor is configured to determine that the discount is available by determining at least one of: (i) whether a payor for the insurance plan is excluded, (ii) whether the customer is of the appropriate age, (iii) whether the pharmacy computer is associated with a participating provider, or (iv) whether the drug is included on an eligible list of drugs.

10. The system of claim 7, wherein the discount is a percentage discount, a flat discount amount, or a variable discount amount.

11. The system of claim 10, wherein the discount is a variable discount amount that enables a specification of a maximum customer amount payable for the drug.

12. The system of claim 7, wherein the processor is configured to transmit at least a notice of availability of the discount to the pharmacy computer by transmitting at least a portion of the coverage information for the claim.

13. The system of claim 7, wherein the processor is further configured to execute the computer-executable instructions to:
   apply the discount to reduce the amount payable by the customer, wherein the transmitted notice of availability includes the reduced amount payable by the customer.

14. The computer-implemented method of claim 1, further comprising:
   applying the discount to reduce the amount payable by the customer, wherein the transmitted notice of availability includes the reduced amount payable by the customer, wherein the prior step is performed by one or more computers.

15. A system, comprising:
   means for receiving an insurance claim from a pharmacy computer, wherein the insurance claim is for a drug requested by a customer;
   means for routing the insurance claim to an adjudication engine for benefits processing;
   means for receiving, from the adjudication engine, insurance coverage information for the insurance claim, wherein the insurance coverage information indicates an amount payable by an insurance plan and an amount payable by the customer;
   means for determining that a discount is available to reduce the amount payable by the customer, wherein the discount is funded by a pharmaceutical entity, wherein an amount of the discount is based at least in part on the amount payable by the customer; and
   means for transmitting at least a notice of availability of the discount to the pharmacy computer.

* * * * *